United States Patent
Matherly et al.

(10) Patent No.: US 6,786,963 B2
(45) Date of Patent: Sep. 7, 2004

(54) PAVING COMPOSITIONS AND METHODS FOR THEIR USE

(75) Inventors: Ronald M. Matherly, Sugarland, TX (US); William H. Steiner, The Woodlands, TX (US)

(73) Assignee: BJ Services Company, Houston, TX (US)

(*) Notice: Subject to any disclaimer, the term of this patent is extended or adjusted under 35 U.S.C. 154(b) by 147 days.

(21) Appl. No.: 10/185,802

(22) Filed: Jun. 27, 2002

(65) Prior Publication Data

US 2003/0061968 A1 Apr. 3, 2003

Related U.S. Application Data

(60) Provisional application No. 60/301,535, filed on Jun. 27, 2001.

(51) Int. Cl.$^7$ .............................. C08L 95/00; B05D 5/10
(52) U.S. Cl. ............................... 106/281.1; 106/284.4; 427/138
(58) Field of Search ................... 106/281.1, 284.4; 427/138; 564/152, 155

(56) References Cited

U.S. PATENT DOCUMENTS

| 4,430,127 A | | 2/1984 | Dalter et al. ............... 106/273 |
|---|---|---|---|
| 4,430,465 A | * | 2/1984 | Abbott ........................ 524/64 |
| 4,443,127 A | | 4/1984 | de Leeuw .................... 403/175 |
| 4,447,269 A | | 5/1984 | Schreuders et al. ......... 106/277 |
| 4,462,840 A | | 7/1984 | Schilling et al. ............. 106/277 |
| 4,561,901 A | * | 12/1985 | Schilling ..................... 106/277 |
| 4,721,529 A | | 1/1988 | Mullins ....................... 106/281 |
| 4,806,166 A | | 2/1989 | Schilling et al. ........ 106/284.06 |
| 4,957,560 A | * | 9/1990 | Schilling ..................... 106/277 |
| 5,019,610 A | | 5/1991 | Sitz et al. ...................... 524/61 |
| 5,443,632 A | | 8/1995 | Schilling ..................... 106/277 |
| 5,587,498 A | | 12/1996 | Krogh et al. .................. 554/69 |

FOREIGN PATENT DOCUMENTS

| CH | 624698 | * | 8/1981 |
|---|---|---|---|

OTHER PUBLICATIONS

Derwent abstract of CH624698, Aug. 1981.*
Derwent abstract of DE1543909, 1968, no month available.*

* cited by examiner

Primary Examiner—Helene Klemanski
(74) Attorney, Agent, or Firm—Howrey Simon Arnold & White, LLP

(57) ABSTRACT

A paving composition is disclosed comprising a bituminous material, such as asphalt, and a reaction product of at least one polycarboxylic acid reacted with at least one polyamine. The composition preferably is substantially free of water. The reaction product can be a diamide compound. The paving composition can further include mineral aggregate. The paving composition can be used in applications such as road construction or repair.

24 Claims, No Drawings

PAVING COMPOSITIONS AND METHODS FOR THEIR USE

CROSS REFERENCE TO RELATED APPLICATIONS

The present application claims priority to U.S. Provisional Patent Application Serial No. 60/301,535 filed Jun. 27, 2001, the contents of which are incorporated herein by reference.

FIELD OF THE INVENTION

The invention relates to a paving composition for use in road construction and related applications. In particular, the invention relates to an asphalt-based paving composition with an anti-stripping agent to improve the adhesion of the asphalt to mineral aggregate.

BACKGROUND OF THE INVENTION

Bituminous materials, such as asphalt, have been used in the building of roadways, driveways, and the like. In addition to asphalt, mineral aggregates are also used to increase the strength and to prolong the life of such surfaces. In road construction, bitumen-aggregate mixtures are applied to the road surface. These bitumen-aggregate mixtures generally can be obtained by mixing anionic or cationic asphalt emulsions with a mineral aggregate, such as stone chips, gravel or sand, or by mixing free flowing heated asphalt (asphalt cement) with a pre-dried mineral aggregate, by a hot mix process. The pre-dried aggregate can also be mixed with asphalt diluted in a hydrocarbon solvent, known as cutback asphalt.

The quality of the road surface is generally dependent upon the strength of the bonds between the asphalt and aggregate after setting of the composition. Poor service performance is, in part, due to poor adhesion between the asphalt and aggregate, resulting in the stripping off of the asphalt from the aggregate surface.

Asphalt compositions have relatively poor adhesion to mineral aggregates in the presence of water. Since the aggregate is preferentially wetted by water, even if the aggregate is dry at the time it is blended with the asphalt, the eventual penetration of water into the composition reaches the aggregate and interferes with the bond between the aggregate and the asphalt. The result of this stripping is flaked pavement and pot holes. Stripping problems also generally occur if the aggregate is poorly dried, if sandy carbonate aggregate containing a large amount of quartz particles is used, if carbonate aggregate is covered with dust, or if igneous (silicate) aggregates, such as granite, diorite, gabbro, diabase, or basalt, that strip in the presence of external water are used. To avoid such failures, adhesion improving agents known as "anti-stripping agents" are commonly added to the asphalt. Before the mixing operation, these agents are added to the bituminous binder to reduce its surface tension and to induce on the binder an electrical charge opposite to that of the aggregate surface. Lower surface tension gives improved wettability of the aggregate, and charge reversal enhances bond strength by increasing Coulomb's attractive forces.

Cationic substances, particularly amines, have been traditionally used as anti-stripping agents. The cationic substances increase the hydrophobicity of the aggregate, making the aggregate resistant to the penetration of water so that water seeping into the asphalt does not tend to destroy the bond between the asphalt and the aggregate. The addition of the cationic substances tends to make the aggregate sufficiently water resistant that a good bond with the asphalt is formed. Among the cationic materials which have been used as adhesion promoters with asphalt are primary alkyl amines (such as lauryl amine and stearyl amine) and alkylene diamines (such as the fatty alkyl substituted alkylene diamines). Because these amines may rapidly lose their activity when combined with asphalt and stored at elevated temperatures for an extended period, it has therefore been necessary to combine the amine with the asphalt at the work site when the asphalt is combined with the aggregate, which in practice presents difficulties in obtaining a homogeneous mixture. It is also noted that these amines are generally corrosive and may have an unpleasant smell.

Various asphalt formulations have been reported in attempts to enhance the properties of paving compositions while avoiding the above-described difficulties. U.S. Pat. No. 4,447,269 offers cationic oil in water type bituminous aggregate slurries. The emulsion comprises bitumen and a reaction product of a polyamine and a polycarboxylic acid, and water. Lime or cement can be added to reduce the setting time of the mixture.

U.S. Pat. No. 4,721,529 suggests the preparation and use of asphalt admixtures with the reaction product of an amine antistrip and an acid salt. The acid salt is a divalent or trivalent metal salt of an inorganic acid.

U.S. Pat. No. 5,443,632 suggests cationic aqueous bituminous emulsion-aggregate paving slurry seal mixtures. The emulsifier is the product of reaction of polyamines with fatty acids and rosing, and a quaternizing agent.

U.S. Pat. No. 4,806,166 proposes preparation of an aggregate comprising asphalt and an adhesion improving amount of an anti-stripping agent comprising the aminoester reaction product of a tall oil fatty acid and triethanolamine. The reaction product is of low viscosity, has good coating performance, and is inexpensive.

U.S. Pat. No. 5,019,610 offers an asphalt composition comprising a blend of a thermoplastic rubber polymer and a fatty dialkyl amide, and asphalt cement. The preparation method requires only gentle stirring. The amide has a $C_6$–$C_{22}$ alkyl group attached to the carbonyl, and two $C_1$–$C_8$ alkyl groups attached to the amide nitrogen. The compositions offer good viscosities at relatively low residue percentages. The compositions are offered for use in road paving, asphalt roofing cements, mastics, moisture barriers, joint and crack fillers, and sheeting.

U.S. Pat. No. 4,430,127 suggests preparation of a bitumen and epoxylated polyamine composition. The compositions provide improved adhesion between aggregate materials and the bitumen material. At least two of the amino nitrogen atoms are separated by six carbon atoms.

U.S. Pat. No. 4,462,840 proposes use of a cation-active emulsifier which is the product of a polyamine and polycarboxylic acids. The emulsifier is useful in producing aqueous bituminous emulsion-aggregate slurries.

Although significant effort has been spent on improving the adhesion between mineral aggregates and asphalt, there continues to exist a need for paving compositions with improved adhesion between mineral aggregate and asphalt. Preferably, the paving compositions should not have an unpleasant odor or smell.

SUMMARY OF THE INVENTION

Paving compositions comprising a bituminous material such as asphalt and an amide compound are disclosed. The amide is preferably a diamide. The compositions can further comprise mineral aggregates or other materials suitable for use in paving applications. The compositions can be used in new road construction, or in road repair applications.

DETAILED DESCRIPTION OF THE INVENTION

Embodiments of the invention provide a paving composition and methods for making and using the composition. The paving composition comprises a bituminous material, such as asphalt, and a reaction product of at least one polycarboxylic acid reacted with at least one polyamine or amine. Preferably, the composition is substantially free of water. The composition is preferably not an emulsion. The paving composition can further include mineral aggregate mixed with the bituminous material and the reaction product. Preferably, the reaction product of the polycarboxylic acid and the polyamine or amine is an amide compound. The amide compound includes one or more amide functional groups:

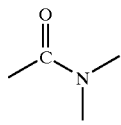

Preferably, the amide compound is a diamide or a compound including multiple amide functional groups (i.e., three or more amide functional groups). The term "multiamide compound" used herein refers to an amide compound with two, three, four, five, six, seven, or more amide groups per molecule. In some embodiments, polymeric amide or polyamide is used as an anti-stripping agent; in other embodiments, polymeric amide or polyamide is substantially absent in a paving composition.

It is found that an amide compound, such as a diamide compound, can be used to enhance the adhesion between a bituminous material and mineral aggregate without using water. Thus, it functions as an anti-stripping agent. To make a paving composition, an amide compound is mixed with a bituminous material without adding water to the mixture. Mineral aggregates can be added to the mixture. After sufficient blending, the paving composition is ready for use. Preferably, the mineral aggregates are dried to remove moisture before being blended with the mixture. By substantially eliminating the presence of water in the paving composition, the adhesion between the mineral aggregate and the bituminous material is improved. Although it is preferred not to use water in formulating the paving composition, a small amount of water may be tolerated in the paving composition. In some instances, up to about 5 wt. % of water in a paving composition may be acceptable. Preferably, the water content is kept lower than about 4%, about 3%, about 2%, about 1% or about 0.5% by weight of the total composition.

Any bituminous material may be used in embodiments of the invention. Examples of bituminous materials include, but are not limited to, asphalt, tar, pitch, etc. A bituminous material includes, but is not limited to, any of various mixtures of hydrocarbons or other substances, occurring naturally or obtained by distillation from coal or petroleum, that are used for surfacing roads or for waterproofing. A preferred bituminous material is asphalt. Chemically, asphalts are complex aggregations of rather large aliphatic and cyclic hydrocarbon molecules. Besides the hydrocarbon content, additional constituents in asphalts may include oxygen, sulfur, and nitrogen (often in substantial quantities) and iron, nickel, and vanadium (present usually in trace quantities). Any amount of asphalt may be used. Preferably, asphalt is present in an amount of about 2% to about 10% or about 4% to about 8% by weight of mineral aggregate, and an anti-stripping agent is present in an amount of about 0.1% to about 5% or about 1% by weight of asphalt.

Any aggregate suitable for use in road construction or related applications may be used in embodiments of the invention. Although it is referred to as "mineral aggregate" herein, it need not be based on minerals. Suitable aggregate can be hydrophilic or hydrophobic, depending on the nature of the material. While the aggregate can include various mineral materials, such as cinders or stags, typically the aggregate is of natural origin, such as sand, rock, or the like, typically to the localities where the roads are being built, For example, limestone, dolomite, silica, sedimentary, metamorphic, or igneous rocks of various kinds are regularly used in road construction or related applications. Other types of aggregate, such as gravel, granite, trap rock, sandstone, etc., may also be used. Additional suitable aggregate is known in the art. Mineral aggregate may be present in any amount. Generally, mineral aggregate is about 80% to about 99% by weight of a paving composition, preferably from about 88 wt. % to about 95 wt. %, and more preferably from about 90 wt. % to 95 wt. %.

In formulating a paving composition, various additives may be used. For example, polymers, metal salts, polyamines, acids, petroleum hydrocarbon resins, etc., may be used in addition to a bituminous material, mineral aggregate, and an amide compound. These additives are, for example, disclosed in the following U.S. Pat. Nos. 3,868,263; 4,443,127; 4,447,269; 4,462,840; 4,721,529; 4,806,166; 5,109,610; 5,443,632; and 5,587,498. However, in some embodiments, the paving composition is substantially free of a polymer, such as an alkadiene-vinylarene copolymers and thermoplastic rubber polymers. In other embodiments, the paving composition is substantially free of metal salts, such as a divalent or trivalent metal salt of an inorganic acid. However, the substantial absence of these compounds do not necessarily mean they are absent in all embodiments of the invention.

Any amide compound which can promote the adhesion between a bituminous material and mineral aggregate may be used in embodiments of the invention. An amide compound refers to those co pounds which include at least one amide functional group. Preferably, an amide compound with two, three, four, five, six, seven, eight, nine, ten, or more amide functional groups is used in embodiments of the invention. A diamide compound can be present in a paving composition at various amounts such as about 0.1 wt. % to about 10 wt. %. about 0.5 wt. % to about 5 wt. %, 0.5 wt. % to about 2 wt. %, or about 0.8 wt. % to about 1 wt. %.

One class of suitable diamide compounds are represented by Formula 1 below. The diamide compounds can be made by reacting a dicarboxylic acid with a polyamine according to the following reaction scheme.

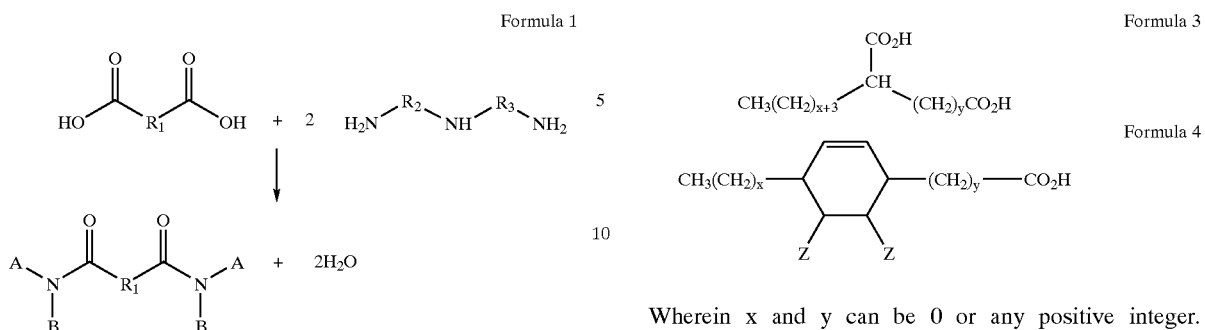

Formula 1

In the above scheme, $R_1$ can be any divalent hydrocarbyl group. The hydrocarbyl group may further include one or more functional substituents, such as a carboxylic group. Preferably, $R_1$ is a branched or straight-chain alkyl group or aromatic or alkylaromatic group, preferably with from about 2 to about 54 carbon atoms per group. $R_2$ and $R_3$ in Formula 1 can be the same or different group, which is a branched chain alkyl group with from about 1 to about 6 carbon atoms or a straight-chain alkyl group with from about 1 to about 6 carbon atoms. Alternatively, each $R_2$ and/or $R_3$ can be —R—NH—R— in which each R can be independently a branched or straight-chain alkyl group with from about 1 to about 6 carbon atoms. Additionally, $R_2$ and/or $R_3$ can be an aromatic or alkylaromatic group. In some embodiments, $R_2$ and/or $R_3$ can also be the same as $R_1$. Moreover, $R_1$ and $R_2$ and/or $R_3$ can be any organic functional group consistent with the stability of the resulting diamide molecule.

The resulting amide compound in Formula 1 may contain secondary or tertiary amide groups or both. The secondary amine is more reactive than the primary amine, but in the case of $R_2$ and $R_3$ being any hydrocarbon (not —R—NH—R) there are twice as many primary amines present for the reaction. Depending on whether the primary amine or the secondary amine group reacts with the carboxylic acid, slightly different products will be obtained. If the primary amine reacts with the carboxylic acid either A or the B component will be a hydrogen atom (making the product a secondary amide) while the other component will be the rest of the polyamine. If the secondary amine reacts with the carboxylic acid either A or B will be —$R_2$—$NH_2$ while the other component will be —$R_3$—$NH_2$, making the resulting amide a tertiary amide. The thermodynamically preferred reaction is to form tertiary amides, however, depending on the reaction method and conditions, as well as what $R_2$ and $R_3$ are, the amount of secondary to tertiary amide can not be controlled. The products can be obtained pure, or as a mixture of products.

As described above, a diamide can be prepared by reacting a diacid with a polyamine. Any diacid that is capable of forming a diamide with an amine compound may be used. One class of suitable diacids is represented by Formula 2 below.

Formula 2

Preferred diacids are represented by Formula 3 and Formula 4 below.

Formula 3

Formula 4

Wherein x and y can be 0 or any positive integer. Preferably, x and y are integers from 3 to 9, x+y=12. Each Z in Formula 4 may be the same or different group, which is a carboxylic acid group or hydrogen, provided that both Zs are not hydrogen at the same time. In other words, at least one Z is a carboxylic acid group. In some embodiments, both Zs may be a carboxylic acid group (i.e., making the compound of Formula 4 a triacid).

In some embodiments, the diacid is a $C_{21}$ carboxylic acid available as "WESTVACO 1550" from Westvaco of Charleston Heights, S.C. This $C_{21}$ carboxylic acid is represented by Formula 5 and Formula 6 below. The molecule of Formula 6 is an isomer of the molecule of Formula 5.

Formula 5

Formula 6

The polycarboxylic acids are obtained by reaction of carbon monoxide and water with an unsaturated acid, preferably oleic acid, as described by Reppe and Kroper, in Annalen der Chemie, 582: 63–65 (1953) in the case of Formula 3, and by Diels-Alder addition of acrylic, methacrylic, fumaric or maleic acid to polyunsaturated fatty acids with conjugated double bonds in the case of Formula 4, forming a cyclohexane structure. These acids are referred to as C19-dicarboxylic acid, C21-dicarboxylic acid and C22-tricarboxylic acid. Acids of this type are disclosed, for example, in U.S. Pat. Nos. 3,753,968 and 3,899,476 to Ward and U.S. Pat. No. 4,081,462 to Powers et al.

Other suitable polyacids and sources thereof include, but are not limited to, crude dimer-trimer acids such as "DTC-195," "DTC-298," "DTC-409," "DTC-295," "DTC-275," "DTC-155 dicarboxylic acids derived from fatty acids such as "DIACID 1550" (monocyclic C21 dicarboxylic acid); and "TENAX 2010" maleated tall oil fatty acid, all from Westvaco, P.O. Box 70848, Charleston Heights, S.C. 29415-0840. Other examples include, but are not limited to, "SYLVADYM MX," "SYLVADYM T-17," "SYLVADYM T-18," "SYLVADYM T-22," "SYLVADYM T-35," "ARIZONA FA-7001" and "ARIZONA FA-7002" all available from Arizona Chemicals, 1001 East Business Highway 98, Panama City, Fla. 32401.

Suitable polycarboxylic acids are not limited to diacids. Carboxylic acids with three or more carboxylic acid groups may also be used. These acids can be produced from fatty acids, other carboxylic acids, carboxylic acid derivatives, alkylene or aryl diisocyanates, or mixtures thereof. These acids may include about 16 to about 36 carbon atoms per molecule, or from about 24 to about 54 carbon atoms per molecule. Polycarboxylic acids with about 4 to about 42 carbon atoms per molecule may also be used. In some embodiments, polycarboxylic acids may result from dimerization or trimerization of an acid, such as linoleic acid and oleic acid. These polycarboxylic acids may also be referred to as "dimer acids" or "trimer acids". For example, linoleic acid may dimerize via Diels Alder reaction, and oleic acid may dimerize over natural acid clay catalysts, such as montmorillonite. Therefore, in some embodiments, suitable polyacid materials may contain mixtures of dimer, trimer and tetramer groups. For example, dimer-trimer products (e.g., Westvaco "DTC"-series acids) may contain mixtures of dimer, trimer and tetramer groups.

Any amine compound or polyamine compound that can react with a polycarboxylic acid to produce an amide compound may be used in embodiments of the invention. One class of suitable polyamines is represented by Formula 7 below.

Formula 7

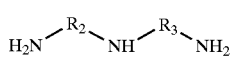

As noted previously, $R_2$ and $R_3$ can be the same or different, and can be an alkyl group or a functional group containing an amine moiety, such as R—NH—R in which each R is an alkyl group. Therefore, Formula 7 encompasses triamines, tetraamines, and any other higher amines, both straight-chained or branched. Suitable polyamines include, but are not limited to, alkylene polyamines, polyalkylene polyamines, aromatic polyamines, and mixtures thereof Examples of suitable polyalkylene polyamines include, but are not limited to, polyethylene and/or piperazine-based polyamines, such as diethylene triamine ("DETA"), triethylene tetraamine ("TETA"), tris-(2-aminoethyl) amine ("branched TETA"), piperazinylethylethylenediamine ("PEEDA"), bis-(2-aminoethyl) piperazine ("bis AEP"), tetraethylenepentamine ("TEPA"), pentaethylene hexamine, aminoethyl-triethylenetetramine ("AETETA"), aminoethylpiperazinyltheyl-ethylenedianiine ("AETETA"), piperazinylethyl-diethylenetriamine ("PEDETA"), piperazinylethyl-hexyleneamine ("PEHA"), bis-hexamethylenetriamine ("BHMT"), and mixtures thereof Such compounds are available from suppliers such as Dow U.S.A. Chemical and Metals Department of Dow Chemical, Midland, Mich.; Bossco Industries, Inc., Houston, Tex. (e.g., TETA and higher ethyleneamine homologs available as "B-AMINE 10-A" from Bossco). Other examples of suitable types of polyamines include, but are not limited to, polyamines available from BASF Corporation, Air Products & Chemical, Inc. and Molex Company, Inc., Athens, Ala.

Triethylene tetraamine and diethylene triamine are preferred polyamines, which are represented by Formula 8 and Formula 9 below.

Formula 8

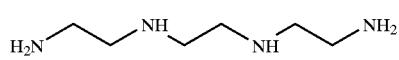

Formula 9

Examples of suitable aromatic polyamines include, but are not limited to, the compounds represented by Formula 10-13 below.

Formula 10

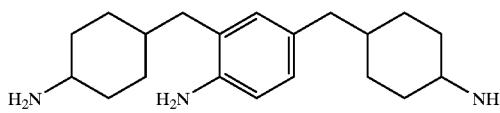

Formula 11

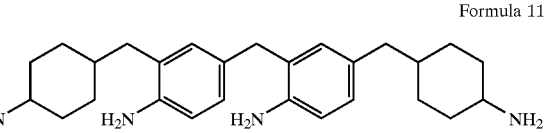

Formula 12

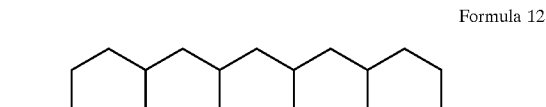

Formula 13

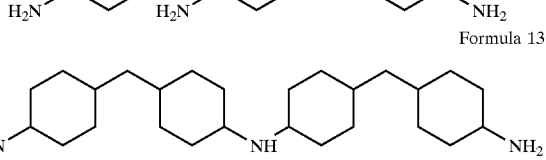

When a polycarboxylic acid is heated with a polyamine, a variety of reaction products may be obtained. For example, by blending two moles of diethylene triamine with one mole of $C_{21}$ dicarboxylic acid, a bis-diethylene diamine salt is formed, which upon heating to about 200° C. forms a diamidoamine of isomer Formulae 14A and 14B.

Formula 14A

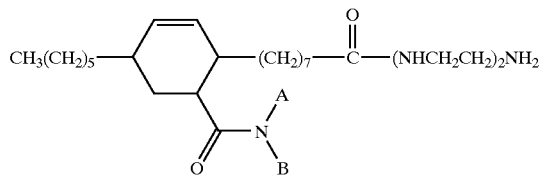

Formula 14B

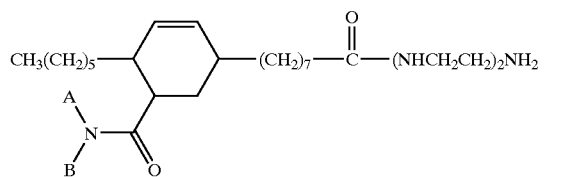

In Formulae 14A and 14B, when A is H, B is $(CH_2)_2NH(CH_2)_2NH_2$; and when A is $(CH_2)_2NH_2$, B is $(CH_2)_2NH_2$. Additionally, isomers of these side chains can be used or obtained.

Such a diamidoamine can be used as an anti-stripping agent to enhance the adhesion between asphalt and mineral aggregates. However, when the reaction mixture is heated, there are other competing reactions. For example, the diamidoamine of Formula 14 may undergo a ring closure to form an amidoimidazoline structure which is represented by Formulae 15A and 15B below.

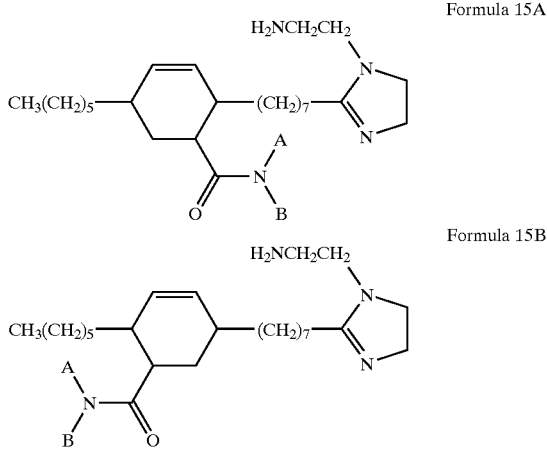

Formula 15A

Formula 15B

In Formulae 15A and 15B, when A is H, B is $(CH_2)_2NH(CH_2)_2NH_2$; and when A is $(CH_2)_2NH_2$, B is $(CH_2)_2NH_2$. Additionally, isomers of these side chains can be used or obtained.

Prolonged heating of the compound of Formula 15A or 15B from about 230° C. to about 280° C. yields a diimidazoline of Formula 16A or 16B below.

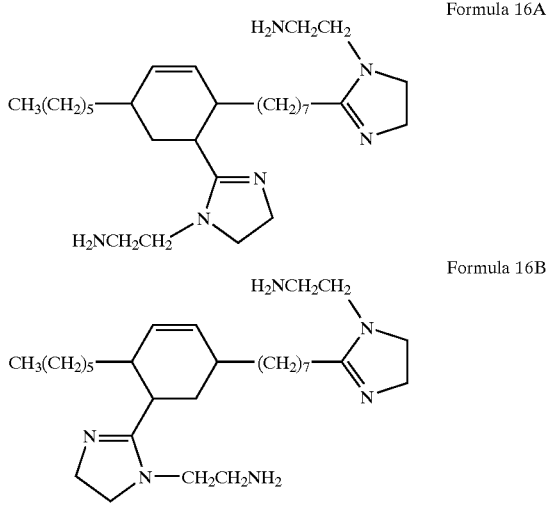

Formula 16A

Formula 16B

When a mixture of two moles of diethylene triamine and one mole of $C_{21}$ dicarboxylic acid is heated slowly, the reaction product may be the diamidoamine of Formula 14A or 14B, the amidoimidazoline of Formula 15A or 15B, the diimidazoline of Formula 16A or 16B, or a mixture thereof. Such reaction products may be used as an anti-stripping agent in embodiments of the invention. Although the reaction products are exemplified by the reaction of a $C_{21}$ dicarboxylic acid and a diethylene triamine, similar reaction products may be made with other types of polycarboxylic acids reacted with other types of polyamines. For example, $C_{19}$ polycarboxylic acids and $C_{22}$ polycarboxylic acids undergo similar chemical reactions as $C_{21}$ polycarboxylic acids when reacted with a polyamine.

Other polyamines may or may not undergo ring closure reactions to form amidoimidazolines or diimidazolines. For example, the formation of amidoimidazolines is limited to polyethylene amines and polyamines characterized by at least one ethylene diamine functional group with at least three hydrogens attached to the two nitrogens. Compounds of this group which are able to give both amidoamines and amidoimidazolines are: ethylene diamine, diethylene triamine, triethylene tetraamine, tetraethylene pentamine, pentaethylene hexamine, and higher homologues-N-aminoethyl propane diamine, N,N-diaminoethyl propane diamine and the N-aminoethyl or N,N-diaminoethyl substituted butane diamines, pentane diamines and hexane diamines, and N-hydroxy ethyl ethylene diamine. These compounds have either the general formula:

$$H_2NCH_2CH_2NHR;$$

wherein

R=—H, —$CH_3$, —$C_2H_5$, —$C_3H_7$, —$CH_2CH_2OH$, or —$(CH_2CH_2NH)_xH$; and x=1,2,3,4,5,6,7,8,9, or 10.

or $$R_1R_2N(CH_2)_yNHR_3;$$

wherein $R_1$=—H, —$CH_3$, —$C_2H_5$, —$C_3H_7$, or —$CH_2CH_2NH_2$;

$R_2$=—H, —$CH_3$, —$C_2H_5$;

$R_3$ —H, —$CH_3$, —$C_2H_5$, —$C_3H_7$, or —$CH_2CH_2NH_2$; and y=2,3,4,5, or 6.

Amines capable of forming amidoamines but not imidazolines are: 1,3-diaminopropane, 1,4-diaminobutane 1,5-diaminopentane, 1,6-diaminohexane, piperazine (1,4-diazacyclohexane), N-aminoethylpiperazine, N-hydroxyethyl piperazine, N-aminopropyl-propane diamine-1,3, N-methyl-N-aminopropylpropane diamine-1,3, N,N-dimethylpropane diamine-1,3, N,N-diethyl propane diamine-1,3, N,N-dimethyl-ethylene diamine, N,N-diethyl ethylenediamine; N-aminohexylhexane diamine-1,6.

The reaction products obtained from the reaction between a polycarboxylic acid and a polyamine may be modified by further reaction with reactive oxirane systems (such as ethylene oxide, propylene oxide or butylene oxide). Such reactions are disclosed in U.S. Pat. No. 4,447,269. The resulting modified reactions products may also be used in embodiments of the invention.

The paving composition in accordance with embodiments of the invention may be made by any method known or unknown in the art. For example, a bituminous material may be premixed with a suitable anti-stripping agent (e.g., a diamide compound) to obtain a bituminous mixture. Preferably, the mixing is conducted in the substantial absence of water. Consequently, the bituminous mixture is substantially free of water. Afterwards, mineral aggregates may be mixed with the bituminous mixture to form a paving composition. One or more suitable additives may be added at any stage of the process. Generally, the mixing is conducted at an elevated temperature, for example, from about 250° F. to about 400° F. (about 121° C. to about 204° C.).

The compositions can further comprise a fatty amine, a fatty propane diamine, a fatty amidoamine, a fatty imidazoline, a fatty monoquatenary ammonium salt, a fatty diquatenary diammonium salt, an ethylene glycol polyether of nonyl phenol, an ethylene glycol polyether of dodecyl phenol, or a mixture thereof. The compositions can also further comprise a nitrogen derivative of rosin acid, a nitrogen derivative of kraft lignin, or a mixture thereof.

A paving composition may also be made by mixing a bituminous material, an anti-stripping agent, and mineral aggregates simultaneously, preferably in the substantial absence of water. Such mixing is preferably conducted at an elevated temperature, for example, from about 150° F. to about 400° F. (about 66° C. to about 204° C.). Additional additives may also be added if desired. Still another method, for making a paving composition is to premix an anti-stripping agent with mineral aggregates and then subsequently add a bituminous material to the mixture at an elevated temperature. If desired, an anti-stripping agent may be diluted by a solvent before mixing.

An additional embodiment of the invention is directed towards methods of using the above-described compositions. The paving composition in accordance with embodiments of the invention may be used to construct or repair a road or used in other applications. One method of paving a road comprises obtaining a mixture of a bituminous material and a diamide compound, wherein the mixture substantially lacks water; adding a mineral aggregate to the mixture to prepare a paving composition; and applying the paving composition to a portion of a road. The obtaining step can comprise obtaining the mixture pre-made from a supplier, or mixing the components of the mixture. The applying step can be performed in the repair of an existing road surface, or in constructing a new road surface.

A method of paving a road in accordance with embodiments of the invention can comprise: (1) mixing a bituminous material with a reaction product of at least one, preferably two, polyamines reacted with at least one polycarboxylic acid, the mixing conducted in the substantial absence of water, thereby resulting in a bituminous mixture substantially free of water; (2) adding a mineral aggregate to the bituminous mixture to obtain a paving composition; and (3) applying the paving composition to a portion of a road. Preferably, the reaction product is an amide compound. The applying step can be performed in the repair of an existing road surface, or in constructing a new road surface. In some embodiments, the first and second steps may be completed in one step. In other embodiments, any one of the above steps may be practiced a number of sub-steps. In addition to the methods described herein for making and using a paving composition, other methods, such as those described in U.S. Pat. Nos. 4,447,269; 4,443,127; 4,721,529; and 5,019,610, may also be used in embodiments of the invention with or without modifications.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

WESTVACO 1550 $C_{21}$ dicarboxylic acid (88.0 grams) was reacted with 51.6 grams of diethylene triamine in the presence of 30 ml of xylene. The reaction was carried out over a 6.5 hour period, starting to reflux at 135° C. and ending at 214° C. The reaction product was isolated and purified. The final product was straw colored viscous liquid. Fourier Transformation Infrared Spectroscopy (FTIR) was used to identify the product as an amidoamine.

Example 2

WESTVACO 1550 $C_{21}$ dicarboxylic acid (88.4 grams) was mixed with 26.7 grams of diethylene triamine in the presence of 40 ml of xylene. An additional 10 ml of xylene was added the mixture. The reaction mixture was slowly heated from 58° C. to 185° C. over a 5.5 hour period, starting to reflux at 129° C. and ending at 185° C. The final reaction product was a straw colored viscous liquid. Fourier Transformation Infrared Spectroscopy (FTIR) was used to identify the product as a mixture of amidoamine and imidazoline, with the amidoamine being the majority.

Example 3

The following reactants were added to a reactor in the order described-30 ml of xylene, 88 grams of WESTVACO 1550 $C_{21}$ dicarboxylic acid, and 73.5 grams of triethylene tetraamine. Under agitation, the reaction mixture was heated from 95° C. to 215° C. over a 7.5 hour period. The reaction product was a straw colored viscous liquid. Fourier Transformation Infrared Spectroscopy (FTIR) was used to identify the product as an amidoamine showing some secondary amine.

Example 4

WESTVACO 1550 $C_{21}$ dicarboxylic acid (88.4 grams) was mixed with 92.9 grams of triethylene tetraamine in the presence of 30 ml of xylene. The reaction mixture was heated from room temperature to 210° C. over a 6 hour period. The reaction product was a straw colored viscous liquid. Fourier Transformation Infrared Spectroscopy (FTIR) was used to identify the product as an amidoamine with excess amine present.

Example 5

WESTVACO 1550 dicarboxylic acid (88 grams) was mixed with 93.9 grams of crude triethylene tetraamine (commercially available from Molex Company, Inc., Athens, Ala.) in the presence of 30 ml of xylene. The reaction mixture was heated from room temperature to 203° C. over a 7 hour period. The reaction product was a straw colored viscous liquid. Fourier Transformation Infrared Spectroscopy (FTIR) was used to identify the product as an amidoamine with less secondary amine present.

Example 6

Triethylene tetraamine (71.2 grams) was mixed with 110.1 grams WESTVACO 1500 (which is a mixture of 65% dicarboxylic acid dimers, 15% dicarboxylic acid monomers, and 20–40% dicarboxylic acid trimers ($C_{54}$ and greater)) in the presence of 50 ml of xylene. The reaction mixture was heated from room temperature to 192° C. over a 7.5 hour period. The reaction product was a straw colored viscous liquid. Fourier Transformation Infrared Spectroscopy (FTIR) was used to identify the product as an amidoamine with higher amide content.

Example 7

Six paving compositions were made according to the following procedure: (1) mix 48 µl of an anti-stripping agent with 30 grams of asphalt at 275° F. and mix them for two minutes; (2) add 150 grams of mineral aggregate to the mixture of asphalt and the anti-stripping agent and continue the mixing for two minutes; (3) heat the resulting composition to 275° F. (135° C.) for at least ten minutes; and (4) remix the mixture for two minutes for a total of three times and allow the resulting mixture to set for 24 hours. The remixing step is optional, and its purpose is to ensure proper mixing and uniform heating of the rock with the asphalt and the anti-stripping agent.

The following anti-stripping agents were used: for Sample No. 1, no anti-stripping agent was used, and sample No. 1 is used as control. For Sample No. 2, LOF 65-00 was used as an anti-stripping agent LOF 65-00 is a commercially available anti-stripping product from ARR-Maz Chemicals, and it is a reaction product between polyamines and fatty acids. Sample No. 2 represents an existing commercial product. For Samples Nos. 3–6, the reaction product made in Examples 3–6 was used respectively. Therefore, Samples Nos. 3–6 represent paving compositions in accordance with embodiments of the invention.

The anti-stripping efficacy was evaluated by a boiling water test. In this test, was heated to the boiling temperature. Then 100 grams of a paving composition (e.g. Samples Nos. 1–6) was placed into the boiling water. The sample was boiled in the water for ten minutes and was removed from the boiling water to cool to room temperature. After cooling, residual oil was wiped off the surfaces of the sample. The sample was visually inspected to obtain an estimated stripping percentage. Coverage percentage is 100%—stripping percentage. The higher the coverage percentage, the better the anti-stripping performance. Table 1 below summarizes the obtained data.

TABLE 1

| Sample | Anti-stripping Agent | Coverage Percentage (%) |
| --- | --- | --- |
| 1 | none | not obtained* |
| 2 | LOF65-00 | 80% |
| 3 | Reaction product of Example 3 | 80% |
| 4 | Reaction product of Example 4 | 90% |
| 5 | Reaction product of Example 5 | 90% |
| 6 | Reaction product of Example 6 | 65% |

*the sample fell upon removal from oven.

Example 8

Georgia Pacific MTO-691 rosin acid (113.0 grams) was mixed with 78.1 grams of triethylene tetraamine in the presence of 50 ml of xylene. MTO-691 is a mixed rosin acid and polymerized tall oil with maleic anhydride to form a polymerized acid. The mixture was heated from room temperature to 192° C. in a 5.5 hour period. The mixture started to boil at 136° C. The reaction product was a straw colored viscous liquid characterized as an amidoamine showing secondary amine and lower conversion rate to amide.

Example 9

Georgia MTO-691 (112.5 grams) was mixed with 85.0 grams of triethylene tetraamine in the presence of 50 ml of xylene. The reaction mixture was agitated and heated from room temperature to 190° C. in a 6.75 hour period. The reaction product was a straw colored viscous liquid characterized as an amidoamine showing more secondary amine and even lower conversion rate to amide.

Example 10

WESTVACO 1525 acid (112.5 grams) was mixed with 62.5 grams of triethylene tetraamine from Molex in the presence of 50 ml xylene. WESTVACO 1525 is a mixture of WESTVACO 1550 and 45% tall oil fatty acids. The reaction mixture was agitated and heated from room temperature to 180° C. in a 6 hour period. The reaction product was a straw colored viscous liquid. The product was characterized by FTIR as an amidoamine.

Example 11

Samples 7–13 were made according to the procedure substantially similar to the one described in Example 7, except 9 grams of asphalt were mixed with 12 µl of an anti-stripping agent. Moreover, 141 grams of rock were added to the mixture of asphalt and the anti-stripping agent. Sample 7 did not include an anti-stripping agent and thus was used as control. Sample 8 included LOF65 as an anti-stripping agent. Samples 9–13 included the following anti-stripping agents, respectively: RM 85 concentrate; RM 85 final product; RM 101 in 50% slurry oil; RM 103 in 50% slurry oil; and RM 107 in 50% slurry oil.

RM 85 concentrate was the reaction product made in Example 4. RM 85 final product was RM 85 diluted 50% in slurry oil. Slurry oil is a liquid grade of asphalt. RM 101 was the reaction product made in Example 8; RM 103 Example 9; and RM 107 Example 10.

Samples 7–13 were evaluated by a boiling test as described in Example 7. The higher the percent coverage, the better the performance. Table 2 below summarizes the boiling test results.

TABLE 2

| Sample | Anti-stripping Agent | Coverage Percentage |
| --- | --- | --- |
| 7 | none | 60% |
| 8 | LOF65 | 94% |
| 9 | RM 85 Concentrate | 97% |
| 10 | RM 85 Final Product | 96% |
| 11 | RM 101 (in 50% slurry oil) | 80% |
| 12 | RM 103 (in 50% slurry oil) | 80% |
| 13 | RM 107 (in 50% slurry oil) | 89% |

Example 12

Additional boiling tests were conducted according to the procedure described in Example 11 on Samples 14–19. The boiling test results are presented in Table 3 below.

TABLE 3

| Sample | Coverage Percentage (%) | Anti-Stripping Agent | Remarks |
| --- | --- | --- | --- |
| 14 | 99 | Molex A-180 | It was composed mainly of about 44% pentaethylene hexylamine and 47 hexaethylene heptamine. |
| 15 | 98 | Molex A-744 | It was a reaction product between 4 moles of ethylene oxide and ethylene diamine. |
| 16 | 92 | Unichem 8162 | It was fatty acid polyamide in slurry oil, available from BJ Services, Houston, TX. |
| 17 | 91 | Modified RM107 | It was obtained by reacting RM 107 (see above) with Silquest A-1310 (which is gamma-isocyanatopropyl-triethoxysilane) available from Crompton Corp, CT. |
| 18 | 89 | Biogreen 6011 | It was composed of 70% active modified imidazoline, available from Clearwater, Inc., Pittsburgh, PA, as Alpha-6011. |
| 19 | 87 | LOF-55 | See Example 7. |
| 20 | 68 | Blank | No anti-stripping agent was used. |

Table 3 shows that modified RM 107 and Unichem 8162 had similar performance. Although amine based anti-stripping agents, Molex A-1 80 and Molex A-744, showed better performance, they do not pass the freeze-and-thaw test.

Example 13

A freeze-thaw assay was used to evaluate various compositions for their suitability in asphalt paving applications.

A piece of road surface is constructed as a round disk approximately 1–3 inches thick and 3 inches in diameter. The disk is placed under water, and a vacuum is applied to facilitate water infiltration of the disk. The water impregnated disk is then frozen overnight, and thawed at room temperature the next day. Lateral tensile strength is evaluated by placing the disk in a press, and determining the amount of pressure required to break the sample. Five samples of each composition are tested, and the results averaged. A control sample is prepared using the same composition not subjected to water infiltration and not frozen and thawed.

Table 4 shows the results of five different compositions. The table presents pressures required to break control samples and frozen/thawed samples, both in pounds/mm thickness. Additionally, the table presents recovery strength, which is the frozen/thawed pressure divided by the control pressure, times 100%.

Samples are made of asphalt with the indicated weight percent of additive. Arr-Maz is a commercial product sold by Process Chemicals LLC (Tampa, Fla.); Formula 14 is a diamide made with 580 grams WESTVACO 1550 and 415 grams Triethylene tetraamine (TETA) in the presence of 5 grams aromatic solvent and reacted to completion. The final product is identified by FTIR as an amidoamine. Unichem 8161 is a commercial product sold by BJ Unichem (a division of BJ Services Company; Houston, Tex.) RM39A is a mixture of 50% Unichem 8161, 30% Formula 14, and 20% slurry oil (a solvent filler).

TABLE 4

| Sample | Control pressure | Frozen/thawed pressure | Recovery strength |
| --- | --- | --- | --- |
| Arr Maz (1%) | 7.15 | 6.12 | 85.5% |
| Formula 14 (1%) | 8.69 | 6.85 | 78.8% |
| Formula 14 (0.5%) | 10.72 | 9.65 | 90.0% |
| Unichem 8161 (1%) | 9.18 | 6.96 | 75.8% |
| RM 39A (1%) | 8.00 | 7.63 | 95.4% |

It is desirable that a sample have high control pressure, frozen/thawed pressure, and recovery strength. It is noteworthy that the 0.5% concentration of Formula 14 gave higher pressure and recovery strength values than the 1% concentration sample. The blended RM 39A sample displayed the highest recovery strength value of all samples, suggesting a synergistic effect of combining Formula 14 with other commercial products. As is shown in the Table, 1% Formula 14 gave 78.8% recovery, 1% Unichem 8161 gave 75.8% recovery, while a mixture of the two gave 95.4% recovery.

As demonstrated above, embodiments of the invention provide a paving composition and methods of making and using the composition. Because amines are not used as an anti-stripping agent in some embodiments, the resulting paving composition does not have the smell characteristic of an amine anti-stripping agent. The anti-stripping efficacy of the paving composition in accordance with some embodiments of the invention is comparable to or better than existing commercial products. Therefore, an alternative to the commercial products is provided. Because water is not used in some embodiments of the invention in formulating a paving composition, the adverse effect of water upon the adhesion between mineral aggregates and asphalt is minimized. Therefore, the resulting paving composition should have improved adhesion between the mineral aggregates and asphalt. Additional advantages include, but are not limited to, lower costs, good freeze resistance, simpler application processes, etc. Other advantages and characteristics provided by embodiments of the invention are apparent to those skilled in the art.

While the invention has been described with a limited number of embodiments, they do not represent the only embodiments of the invention. These specific embodiments are not intended, nor should they be construed, to limit the invention as otherwise described herein. Moreover, modifications and variations from the specific embodiments exist. For example, while water is preferred to be absent in formulating a paving composition in some embodiments, it does not preclude the presence of water in other embodiments. Similarly, when water is preferred to be absent in one step, this does not preclude the use of water in other steps in a method. Although a diamide compound is a preferred anti-stripping agent, it should be understood that any amide compound may be used so long as it enhances the adhesion between aggregate and a bituminous material. Diamide compounds preferably are prepared by the reaction between a polycarboxylic acid and a polyamine. This does not preclude the use of other methods to make an amide compound. For instance, U.S. Pat. No. 5,587,498 discloses various synthetic methods for making amide compounds, all of which may be used in embodiments of the invention with or without modification. In addition, polyamide compounds and oligomeric amides may also be used. U.S. patent application Ser. No. 09/736,478, filed on Dec. 13, 2000, entitled "Compositions and Methods for Controlling Particulate Movement in Wellbores and Subterranean Formations," discloses various polyamide compounds which may also be used in embodiments of the invention. The methods of making and using a paving composition are described with respect to a number of steps. These steps may be practiced in any order or sequence so long as they achieve the desired result. It is also possible to combine two or more steps into a single step. Conversely, it is also possible to divide a single step into a number of sub-steps. The appended claims intend to cover all such modifications and variations as falling within the scope of the invention.

What is claimed is:

1. A paving composition comprising a bituminous material and a diamide compound, wherein:

the composition is substantially free of water; and the diamide compound is represented by:

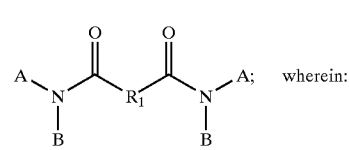

(Formula 1)

if A is hydrogen, B is $R_2NHR_3NH_2$;

if A is $R_2NH_2$, B is $R_3NH_2$;

$R_1$ is a branched or straight-chain alkyl or aromatic or alkylaromatic group; and $R_2$ and $R_3$ are the same or different and are a branched chain alkyl, straight-chain alkyl, or —R—NH—R, in which R is a branched chain alkyl with about 1 to about 6 carbon atoms or a straight-chain alkyl with about 1 to about 6 carbon atoms.

2. The paving composition of claim 1, further comprising a mineral aggregate.

3. The paving composition of claim 1, wherein the bituminous material is asphalt.

4. The paving composition of claim 1, wherein the diamide compound is a reaction product of at least one polyamine reacted with at least one polycarboxylic acid.

5. The paving composition of claim 4, wherein the polycarboxylic acid is represented by Formula 2:

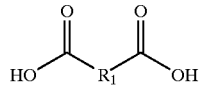

(Formula 2)

wherein $R_1$ is a branched chain alkyl, straight-chain alkyl, aromatic, or alkylaromatic group.

6. The paving composition of claim 4, wherein the polyamine is represented by Formula 7:

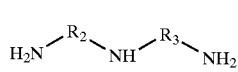

(Formula 7)

wherein $R_2$ and $R_3$ are the same or different and are a branched chain alkyl, straight-chain alkyl, or —R—NH—R, in which R is a branched chain alkyl with about 1 to about 6 carbon atoms or a straight chain alkyl with about 1 to about 6 carbon atoms.

7. The paving composition of claim 2, wherein the diamide compound is present in an amount sufficient to promote adhesion between the bituminous material and the mineral aggregate.

8. The paving composition of claim 2, wherein the diamide compound is present in an amount of about 0.1 wt. % to about 10 wt. %.

9. The paving composition of claim 2, wherein the diamide compound is present in an amount of about 0.5 wt. % to about 5 wt. %.

10. The paving composition of claim 2, wherein the diamide compound is present in an amount of about 0.5 wt. % to about 2 wt. %.

11. The paving composition of claim 2, wherein the diamide compound is present in an amount of about 0.8 wt. % to about 1 wt. %.

12. The paving composition of claim 2, further comprising cement, hydrated lime limestone dust, fly ash, or a mixture thereof.

13. The paving composition of claim 1, further comprising a fatty amine, a fatty propane diamine, a fatty amidoamine, a fatty imidazoline, a fatty monoquatenary ammonium salt, a fatty diquatenary diammonium salt, an ethylene glycol polyether of nonyl phenol, an ethylene glycol polyether of dodecyl phenol, or a mixture thereof.

14. The paving composition of claim 1, further comprising a nitrogen derivative of rosin acid, nitrogen derivative of kraft lignin, or a mixture thereof.

15. A paving composition comprising:
   asphalt;
   a mineral aggregate; and
   a diamide compound, wherein:
   the composition is substantially free of water; and
   the diamide compound is represented by:

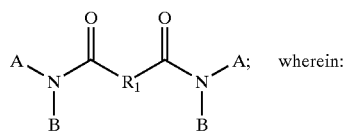

(Formula 1)

if A is hydrogen, B is $R_2NHR_3NH_2$;
if A is $R_2NH_2$, B is $R_3NH_2$;
$R_1$ is a branched or straight-chain alkyl or aromatic or alkylaromatic group; and $R_2$, and $R_3$ are the same or different and are a branched chain alkyl, straight-chain alkyl, or —R—NH—R, in which R is a branched chain alkyl with about 1 to about 6 carbon atoms or a straight-chain alkyl with about 1 to about 6 carbon atoms.

16. A method of preparing a paving composition, the method comprising mixing a bituminous material with a diamide compound in the substantial absence of water to prepare a mixture; wherein the diamide compound is represented by:

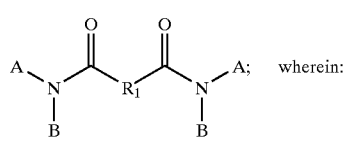

(Formula 1)

if A is hydrogen, B is $R_2NHR_3NH_2$;
if A is $R_2NH_2$, B is $R_3NH_2$;
$R_1$, is a branched or straight-chain alkyl or aromatic or alkylaromatic group; and
$R_2$ and $R_3$ are the same or different and are a branched chain alkyl, straight-chain alkyl, or —R—NH—R, in which R is a branched chain alkyl with about 1 to about 6 carbon atoms or a straight-chain alkyl with about 1 to about 6 carbon atoms.

17. The method of claim 16, further comprising adding a mineral aggregate to the mixture.

18. The method of claim 16, wherein the diamide compound is a reaction product of at least one polyamine reacted with at least one polycarboxylic acid.

19. The method of claim 16, further comprising adding a mineral aggregate during the mixing of the bituminous material and the diamide compound.

20. The method of claim 16, further comprising adding a mineral aggregate after the mixing of the bituminous material and the diamide compound.

21. The method of claim 16, wherein the bituminous material is asphalt.

22. A method of paving a road, the method comprising:
   obtaining a mixture of a bituminous material and a diamide compound, wherein the mixture substantially lacks water;
   adding a mineral aggregate to the mixture to prepare a paving composition; and
   applying the paving composition to a portion of a road;
   wherein the diamide compound is represented by:

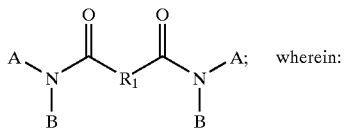

(Formula 1)

wherein:

if A is hydrogen, B is $R_2NHR_3NH_2$;
if A is $R_2NH_2$, B is $R_3NH_2$;
$R_1$ is a branched or straight-chain alkyl or aromatic or alkylaromatic group; and
$R_2$ and $R_3$ are the same or different and are a branched chain alkyl, straight-chain alkyl, or —R—NH—R, in which R is a branched chain alkyl with about 1 to about 6 carbon atoms or a straight-chain alkyl with about 1 to about 6 carbon atoms.

23. A method of paving a road, the method comprising:
mixing a bituminous material with a diamide compound in the substantial absence of water to prepare a bituminous mixture;
adding a mineral aggregate to the bituminous mixture to prepare a paving composition; and
applying th paving composition to a portion of a road;
wherein the diamide compound is represented by:

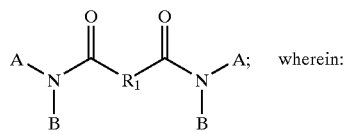

(Formula 1)

wherein:

if A is hydrogen, B is $R_2NHR_3NH_2$;
if A is $R_2NH_2$, B is $R_3NH_2$;
$R_1$ is a branched or straight-chain alkyl or aromatic or alkylaromatic group; and
$R_2$ and $R_3$ are the same or different and are a branched chain alkyl, straight-chain alkyl, or —R—NH—R, in which R is a branched chain alkyl with about 1 to about 6 carbon atoms or a straight-chain alkyl with about 1 to about 6 carbon atoms.

24. The method of claim 23, wherein the diamide is a reaction product of at least one polyamine reacted with at least one polycarboxylic acid.

* * * * *